Figure 1:
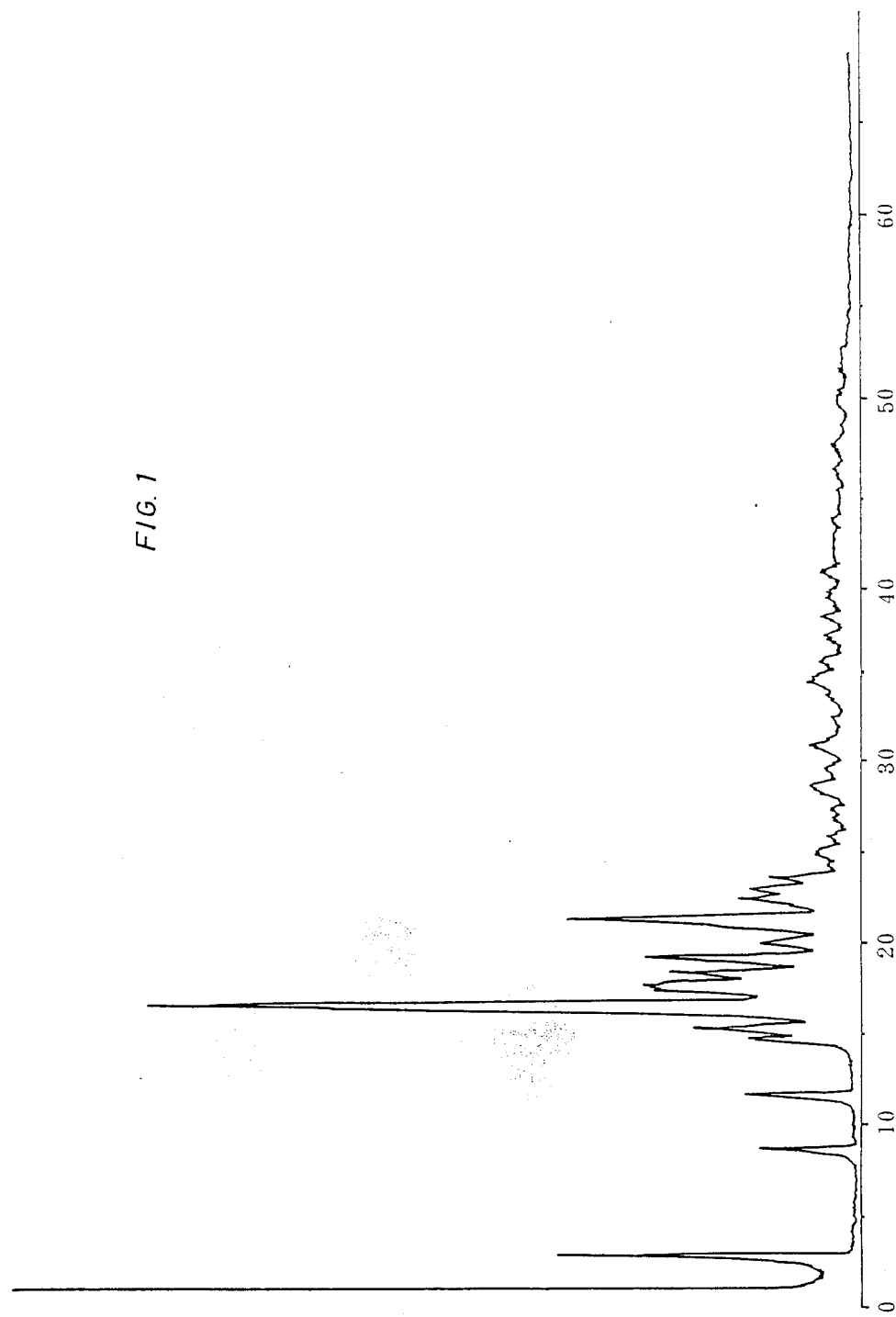

United States Patent [19]

Sasaki et al.

[11] Patent Number: 4,739,080
[45] Date of Patent: Apr. 19, 1988

[54] PURIFICATION OF HYDROXYPHENYLPROPIONIC ACID ESTER

[75] Inventors: Manji Sasaki, Ibaraki; Chinehito Ebina, Minoo; Haruki Okamura, Osaka; Shinichi Yachigo, Toyonaka; Tamaki Ishii, Suita, all of Japan

[73] Assignee: Sumitomo Chemical Company, Limited, Osaka, Japan

[21] Appl. No.: 868,742

[22] Filed: May 30, 1986

[30] Foreign Application Priority Data

Jun. 21, 1985 [JP] Japan ................................ 60-136272
Aug. 29, 1985 [JP] Japan ................................ 60-190457

[51] Int. Cl.$^4$ .......................................... C07D 319/04
[52] U.S. Cl. .................................................... 549/335
[58] Field of Search ............................... 549/343, 335

[56] References Cited

U.S. PATENT DOCUMENTS 4,576,734 3/1986 Ishii et al. ............................ 252/404

FOREIGN PATENT DOCUMENTS 25826 2/1984 Japan.
231089 12/1984 Japan.

Primary Examiner—Nicky Chan
Attorney, Agent, or Firm—Wenderoth, Lind & Ponack

[57] ABSTRACT

Method for the purification of 3,9-bis{2-[3-(3-tert-butyl-4-hydroxy-5-methylphenyl)propionyloxy]-1,1-dimethylethyl} -2,4,8,10-tetraoxaspiro[5.5]undecane, to form crystals having a crystalline structure which, when subjected to Cu-K$_\alpha$ X-ray diffraction, show sharp X-ray diffraction peaks at angles of diffraction, to $2\theta=2.8°$, $2\theta=8.7°$ and $2\theta=11.7°$, by recrystallizing the ester at a temperature lower than 40° C. using as a recrystallization solvent, A C$_5$-C$_{10}$ alicyclic hydrocarbon, which may contain a limited amount of certain other solvents, or using a mixed solvent of a C$_5$-C$_{10}$ aliphatic hydrocarbon and at least one other certain solvent in a certain weight ratio.

5 Claims, 3 Drawing Sheets

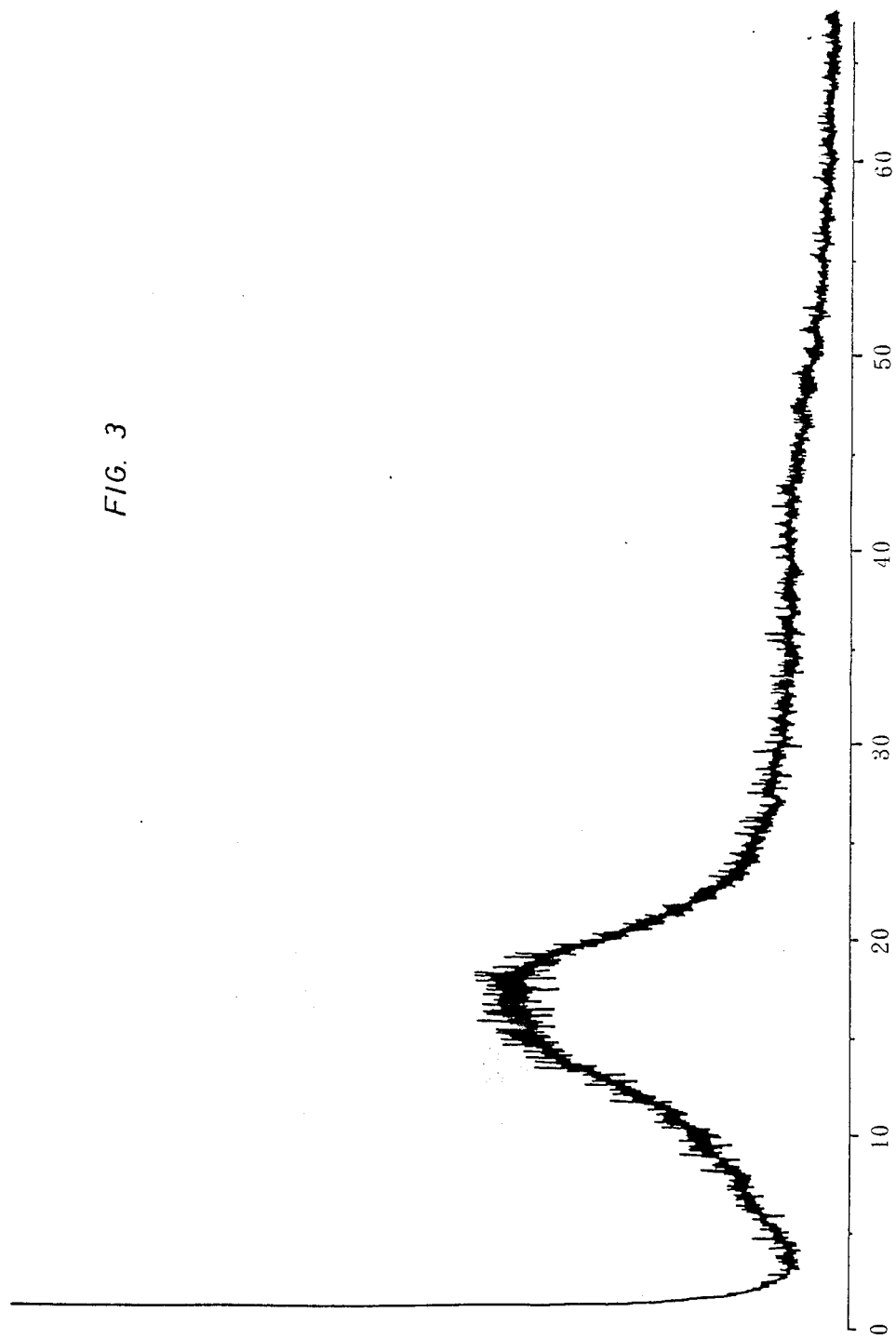

PURIFICATION OF HYDROXYPHENYLPROPIONIC ACID ESTER

The present invention relates to 3,9-bis{2-[3-(3-tert-butyl-4-hydroxy-5-methylphenyl)propionyloxy]-1,1-dimethylethyl}-2,4,8,10-tetraoxaspiro[5.5]undecane (hereinafter referred to as hydroxyphenylpropionic acid ester) represented by the structural formula (I):

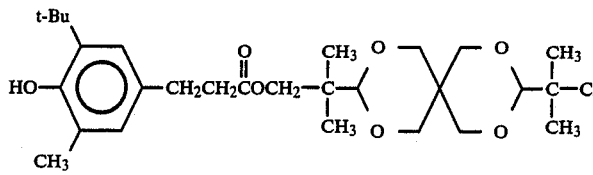

It is well known that the hydroxyphenylpropionic acid ester represented by the structural formula (I) can effectively be used to prevent various kinds of synthetic resin from deterioration such as softening, embrittlement, surface crack, discoloration, etc. caused by the action of heat, light and oxygen at the time of processing and use [Japanese Patent Application Kokai (Laid-open) Nos. 25826/84 and 231089/84]. As such synthetic resins, there may be mentioned polyolefins such as polyethylene, polypropylene, etc., styrene resins such as polystyrene, impact-resistant polystyrene, ABS, etc., engineering plastics such as polyacetal, polyamide, etc., and polyurethane.

For purifying the hydroxyphenylpropionic acid ester represented by the above structural formula (I), the present inventors have previously found a method in which said ester is column-chromatographed on silica gel and the solvent is removed by evaporation to obtain a glassy substance having a melting point of from about 45° C. to about 55° C. (hereinafter referred to as γ-crystal), and a method in which the well-known recrystallization method with n-hexane [disclosed in Japanese Patent Application Kokai (Laid-open) No. 25826/84] for 3,9-bis{2-[3-(3,5-di-tert-butyl-4-hydroxyphenyl)-propionyloxy]-1,1-dimethylethyl}-2,4,8,10-tetraoxaspiro[5.5]undecane represented by the structural formula (II),

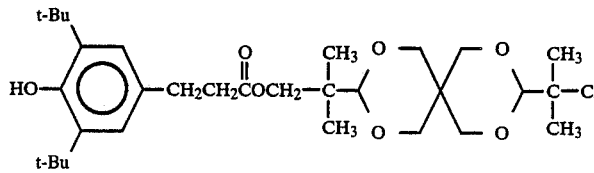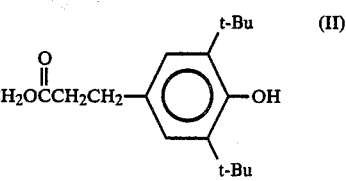

having a similar structure to that of the hydroxyphenylpropionic acid ester represented by the above structural formula (I), is applied as such to said ester of the structural formula (I) to obtain white crystals having a melting point of from about 104° C. to about 109° C. (hereinafter referred to as αβ-crystal).

Figure 2:
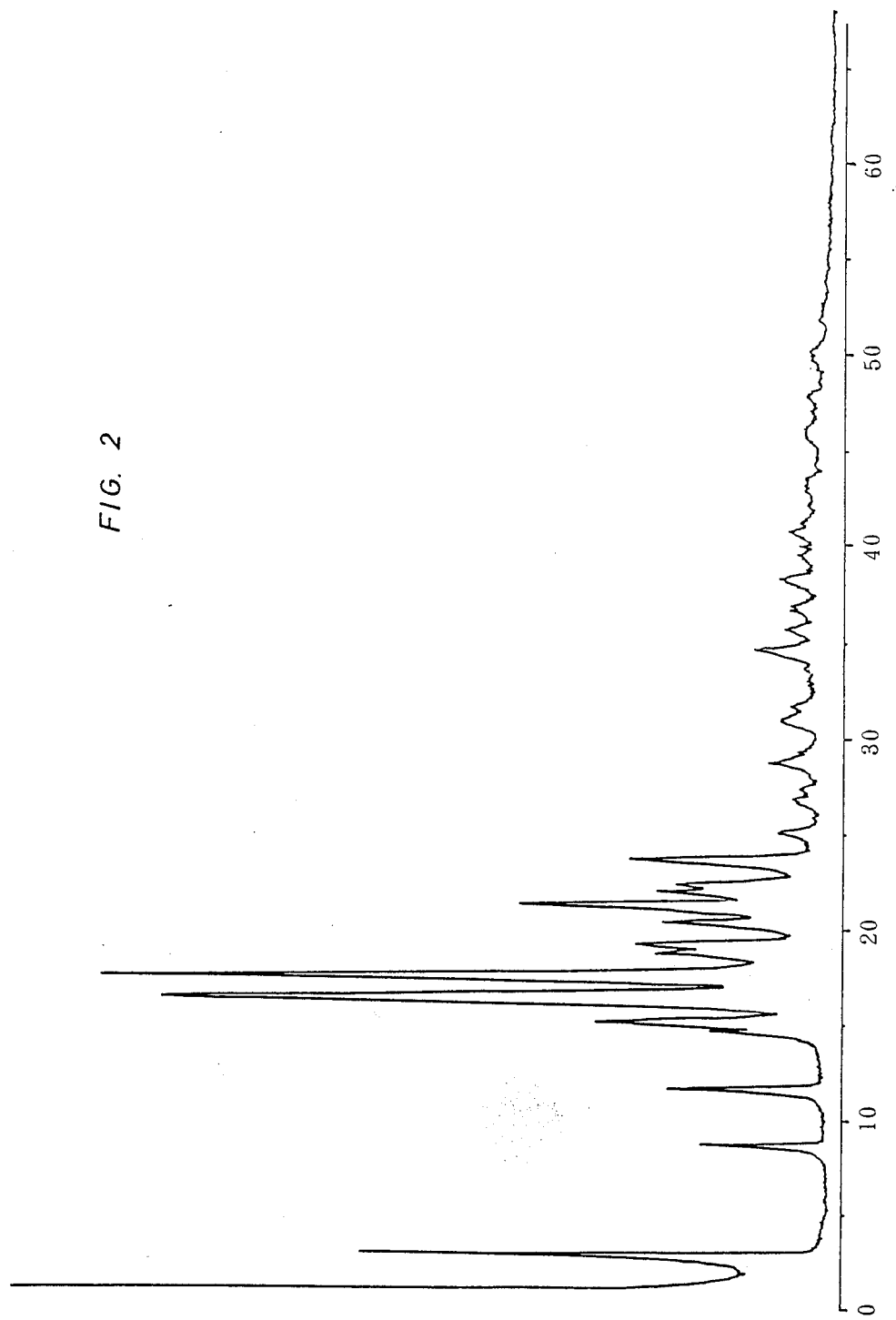

By means of Cu-Kα X-ray diffraction, the present inventors have confirmed that the γ-crystals show an X-ray diffraction pattern having no clear diffraction peak as shown in FIG. 3, and that the αβ-crystals show X-ray diffraction patterns, as shown in Table 1 and FIGS. 1 and 2, having sharp diffraction peaks at angles of diffraction, $2\theta = 2.8°$, $2\theta = 8.7°$ and $2\theta = 11.7°$. Generally, the αβ-crystals seem to be obtained as a mixture of two or more forms having different crystalline structures, and the X-ray diffraction pattern varies as shown by FIGS. 1 and 2 depending upon the mixing ratio of the forms. In any case, however, sharp diffraction peaks are observed at angles of diffraction, $2\theta = 2.8°$, $2\theta = 8.7°$ and $2\theta = 11.7°$.

TABLE 1

| No. | Angle of diffraction 2θ (degree) | Relative strength (%) |
| --- | --- | --- |
| 1 | 2.82 | 38 |
| 2 | 8.72 | 14 |
| 3 | 11.69 | 17 |
| 4 | 14.71 | 15 |
| 5 | 15.25 | 23 |
| 6 | 16.57 | 100 |
| 7 | 17.57 | 31 |
| 8 | 17.78 | 30 |
| 9 | 18.32 | 27 |
| 10 | 19.17 | 32 |
| 11 | 19.92 | 15 |
| 12 | 21.27 | 42 |
| 13 | 22.47 | 18 |
| 14 | 23.04 | 15 |
| 15 | 23.66 | 14 |
| 16 | 24.87 | 6 |
| 17 | 25.95 | 4 |
| 18 | 27.41 | 4 |
| 19 | 28.56 | 7 |
| 20 | 29.64 | 5 |
| 21 | 30.88 | 7 |
| 22 | 34.41 | 8 |
| 23 | 35.52 | 6 |
| 24 | 36.91 | 5 |
| 25 | 38.10 | 5 |
| 26 | 39.21 | 5 |
| 27 | 40.57 | 6 |
| 28 | 41.84 | 4 |
| 29 | 43.45 | 4 |
| 30 | 47.54 | 4 |
| 31 | 49.65 | 3 |

In the purification method as described above, however, when recrystallization is carried out using, for example, n-hexane as a crystallization solvent, scaling of the crystallization apparatus is remarkable, and also the purification effect is low because of a small solubility difference between the ester of the structural formula (I) and impurities contained in the mixture to be purified. This purification method was therefore disadvantageous as a commercial-scale purification method.

Column chromatography is effective as a purification method, but it is disadvantageous for commercial use for economical reasons. Also, in this case, only a glassy substance, called the γ-crystal, having a very low melting point is obtained. Column chromatography, therefore, was unsatisfactory in terms of the property of the desired product.

In view of the above, the present inventors have extensively studied a method for producing the $\alpha\beta$-crystal with high purity in an operationally advantageous manner without formation of the $\gamma$-crystals as well as scales in the crystallization treatment, and as a result, have attained the present invention.

Thus the present invention is to provide the hydroxyphenylpropionic acid ester represented by the structural formula (I) having a crystalline structure which, when subjected to Cu-K$\alpha$ X-ray diffraction, shows sharp X-ray diffraction peaks at angles of diffraction, $2\theta=2.8°$, $2\theta=8.7°$ and $2\theta=11.7°$, by a purification method characterized in that the ester is recrystallized at a crystallization temperature lower than 40° C. using as a recrystallization solvent a $C_5-C_{10}$ alicyclic hydrocarbon (I) which may or may not contain more than 5 wt.% of at least one solvent (II) selected from the group consisting of $C_1-C_8$ alcohols (II-1), $C_3-C_8$ carboxylic acid $C_1-C_4$ alkyl esters (II-2), $C_1-C_3$ aliphatic halides (II-3), $C_6-C_{14}$ aromatic chlorides (II-4), $C_3-C_{13}$ ketones (II-5), $C_2-C_3$ aliphatic nitriles (II-6), $C_2-C_6$ glycols or $C_2-C_6$ glycol $C_1-C_4$ alkyl ethers (II-7), $C_6-C_{14}$ aromatic hydrocarbons (II-8) and $C_4-C_6$ ethers (II-9), or a mixed solvent comprising a $C_5-C_{10}$ aliphatic hydrocarbon (III) and at least one solvent (II) selected from the group consisting of (II-1) to (II-9), the weight ratio of (III) to (II) being 1000 to 5–100.

In the purification method of the present invention, the temperature at which the crystals are formed is important, and when any of the foregoing recrystallization solvents is used, the temperature is preferably lower than 40° C. When the temperature is 40° C. or higher, loss of the ester of the structural formula (I) remaining dissolved in the recrystallization solvent becomes large to lower the crystallization yield, thus being not practical. The crystallization yield is, of course, largely governed by solubility in the recrystallization solvent, and therefore, when an aliphatic hydrocarbon of very low solubility such as n-hexane is used, the crystallization can be effected with a high yield even at a temperature of 40° C. or higher. In this case, however, scaling of the crystallization apparatus is so remarkable that such crystallization is almost impossible in commercial practice.

Referring to the recrystallization solvent to be used in the present invention, the $C_5-C_{10}$ alicyclic hydrocarbons (I) include cyclopentane, cyclohexane, methylcyclohexane, cyclooctane, cyclodecane, etc. The solvents may be used alone or as mixture of two or more of them.

The aliphatic hydrocarbons (III) include n-pentane, n-hexane, n-heptane, n-octane, 2-methylheptane, n-decane, etc. The solvents may be used alone or as mixture of two or more of them.

The $C_1-C_8$ alcohols (II-1) include methanol, ethanol, n-propanol, isopropanol, n-butanol, sec-butanol, tert-butanol, n-pentanol, n-octanol, 2-ethylhexanol, cyclohexanol, glycerin, etc. The $C_3-C_8$ carboxylic acid $C_1-C_4$ alkyl esters (II-2) include methyl acetate, ethyl acetate, n-propyl acetate, n-butyl acetate, ethyl propionate, n-butyl n-hexanoate, dimethyl phthalate, di-n-butyl phthalate, etc. The $C_1-C_3$ aliphatic halides (II-3) include carbon tetrachloride, chloroform, methylene chloride, 1,2-dichloroethane, 1,1,2,2-tetrachloroethane, 1,2-dichloropropane, etc. The $C_6-C_{14}$ aromatic chlorides (II-4) include chlorobenzene, m-dichlorobenzene, o-chlorotoluene, 1-chloronaphthalene, 1-chloroanthracene, etc. The $C_3-C_{13}$ ketones (II-5) include acetone, methyl ethyl ketone, methyl isobutyl ketone, diethyl ketone, acetophenone, benzophenone, etc. The $C_2-C_3$ aliphatic nitriles (II-6) include acetonitrile, propionitrile, etc. The $C_2-C_6$ glycols or their $C_1-C_4$ alkyl ethers (II-7) include ethylene glycol, propylene glycol, diethylene glycol, triethylene glycol or methyl ethers, ethyl ethers, etc. of these glycols. The $C_6-C_{14}$ aromatic hydrocarbons (II-8) include toluene, o-xylene, m-xylene, p-xylene, 1,2,3-trimethylbenzene, 1,2,4-trimethylbenzene, 1,3,5-trimethylbenzene, 1,2,4,5-tetramethylbenzene, ethylbenzene, cumene, o-cymene, m-cymene, p-cymene, o-diisopropylbenzene, m-diisopropylbenzene, p-diisopropylbenzene, naphthalene, anthracene, etc. The $C_4-C_6$ ethers (II-9) include diethyl ether, 1,4-dioxane, tetrahydrofuran, diisopropyl ether, etc.

The solvents (II) represented by (II-1) to (II-9) may be used alone or as mixture of two or more members belonging to the same groups or different groups.

The solvent (II) is used in mixture with the aliphatic hydrocarbon (III) for the purpose of increasing the solubility of the $\alpha\beta$-crystals in the hydrocarbon (III) to improve the purification effect, and preventing scaling of the crystallization apparatus. The amount of the solvent (II) is preferably 5 to 100 parts by weight based on 1000 parts by weight of the hydrocarbon (III). Mixing the solvent (II) in an amount exceeding the above range would result in a further increase in the solubility of the $\alpha\beta$-crystals, which is preferred for purification effect, but it results in a reduction in the crystallization yield, so that it is not preferred in practice.

In the present invention, the $C_5-C_{10}$ alicyclic hydrocarbon (I) may generally be used alone as a recrystallization solvent, but for the purpose of increasing the solubility of the hydroxyphenylpropionic acid ester in the alicyclic hydrocarbon (I) to improve the purification effect, the alicyclic hydrocarbon (I) may contain the above solvent (II) in an amount of not more than 5 wt.%. When the amount exceeds 5 wt.%, the crystallization yield is decreased.

When any of the foregoing recrystallization solvents is used, the amount of the solvent is generally 1 to 10 times by weight based on the material to be subjected to the purification.

In the present invention, the recrystallization operation itself can be carried out by the so far well-known common method without any special limitation. For example, the material to be purified is completely dissolved in the recrystallization solvent of the present invention at the boiling point or a temperature lower than that, seed crystals as nucleus for crystallization are added if necessary, at a temperature less than 40° C., and the solution is stirred at the same temperature to form the crystals. For a further increase in the crystallization yield, the solution is cooled to a much lower temperature if necessary, and the formed crystals are separated from the filtrate by a filter, washed and dried. Of course, it is also possible to apply decoloration treatment with activated carbon, active clay, silica gel, etc. in the course of this operation.

Thus, according to the method of the present invention, the hydroxyphenylpropionic acid ester of the structural formula (I) can be obtained as white crystalline $\alpha\beta$-crystals in a high yield and in good purity without the formation of the $\gamma$-crystals and without operational disadvantages such as scaling of apparatus. The method of the present invention, therefore, is very useful as an industrial method for the purification of the hydroxyphenylpropionic acid ester.

The present invention will be illustrated with reference to the following examples. The percentages (%) in the reference examples, examples and comparative examples are by weight unless otherwise specified.

REFERENCE EXAMPLE 1

To a 500-ml four-necked flask equipped with a stirrer, condenser, thermometer and nitrogen-introducing pipe were added 200.3 g (0.8 mole) of methyl 3-(3-tert-butyl-4-hydroxy-5-methylphenyl)propionate and 60.88 g (0.2 mole) of 3,9-bis(2-hydroxy-1,1-dimethylethyl)-2,4,8,10-tetraoxaspiro[5.5]undecane, and the mixture was formed into solution by heating at 150° C. for 30 minutes with stirring in a nitrogen atmosphere. After adding 2.25 g (0.04 mole) of calcium oxide to this solution, the solution was heated to 190° C. and kept at the same temperature for 6 hours while distilling out formed methanol to complete the reaction.

After completion of the reaction, the reaction solution was diluted with toluene, neutralized with aqueous dilute hydrochloric acid and washed with water. After removing toluene by distillation, 97.1 g of methyl 3-(3-tert-butyl-4-hydroxy-5-methylphenyl)propionate, the starting material present in excess, were distilled off to obtain 148.3 g of a pale yellow highly viscous substance. Analysis of this highly viscous substance showed that it contained 96.4% of 3,9-bis{2-[3-(3-tert-butyl-4-hydroxy-5-methylphenyl)propionyloxy]-1,1-dimethylethyl}-2,4,8,10-tetraoxaspiro[5.5]undecane, the yield of this product being 96.5% based on 3,9-bis(2-hydroxy-1,1-dimethylethyl)-2,4,8,10-tetraoxaspiro[5.5]undecane, and also that said substance contained methyl 3-(3-tert-butyl-4-hydroxy-5-methylphenyl)propionate which was the starting material, and other by-products in the amounts of 1.2% and 2.4%, respectively.

REFERENCE EXAMPLE 2

Procedure was carried out in the same manner as in Reference example 1 except that 2.25 g (0.02 mole) of potassium tert-butoxide was used in place of calcium oxide, and that reaction was completed at 150° C. under a pressure of 5 mmHg. The product was after-treated in the same manner as in Reference example 1. As a result, 92.5 g of methyl 3-(3-tert-butyl-4-hydroxy-5-methylphenyl)propionate, the material present in excess, was recovered, and 145.2 g of a brown highly viscous substance was obtained. Analysis of this highly viscous substance showed that it contained 87.5% of 3,9-bis{2-[3-(3-tert-butyl-4-hydroxy-5-methylphenyl)propionyloxy]-1,1-dimethylethyl}-2,4,8,10-tetraoxaspiro[5.5]undecane, the yield of this product being 85.8% based on 3,9-bis(2-hydroxy-1,1-dimethylethyl)-2,4,8,10-tetraoxaspiro[5.5]undecane, and also that said substance contained methyl 3-(3-tert-butyl-4-hydroxy-5-methylphenyl)propionate which was the starting material, and other by-products in the amounts of 1.4% and 11.1%, respectively.

REFERENCE EXAMPLE 3

Procedure was carried out in the same manner as in Reference example 1 except that 0.46 g (0.02 mole) of lithium amide was used in place of calcium oxide, and that reaction was completed at 150° C. under a pressure of 5 mmHg. The product was after-treated in the same manner as in Reference example 1. As a result, 95.4 g of methyl 3-(3-tert-butyl-4-hydroxy-5-methylphenyl)propionate, the starting material present in excess, was recovered, and 145.8 g of a brown highly viscous substance was obtained. Analysis of this highly viscous substance showed that it contained 88.9% of 3,9-bis{2-[3-(3-tert-butyl-4-hydroxy-5-methylphenyl)propionyloxy]-1,1-dimethylethyl)-2,4,8,10-tetraoxaspiro[5.5]undecane, the yield of this product being 87.5% based on 3,9-bis(2-hydroxy-1,1-dimethylethyl)-2,4,8,10-tetraoxaspiro[5.5]undecane, and also that said substance contained methyl 3-(3-tert-butyl-4-hydroxy-5-methylphenyl)propionate which was the starting material, and other by-products in the amounts of 1.5% and 9.6%, respectively.

The highly viscous substance obtained in Reference example 1 was subjected to Cu-Kα X-ray diffraction, to obtain the X-ray diffraction pattern as shown in FIG. 3. The same X-ray diffraction pattern was also obtained from the highly viscous substances obtained in Reference examples 2 and 3.

EXAMPLE 1

Fifty grams of the highly viscous substance obtained in Reference example 1 were dissolved in 150 g of cyclohexane at 70° C. The resulting solution was rapidly cooled with stirring, and 0.1 g of seed crystals were added at 30° C. Thereafter, the solution was stirred at the same temperature for further 6 hours to form crystals. The formed crystals were filtered off on a glass filter, washed with cyclohexane and dried at 40° C. under reduced pressure to obtain 47.1 g of white crystals having a melting point of 102° to 107° C. Analysis of the white crystals showed that they contained 98.2% of 3,9-bis{2-[3-(3-tert-butyl-4-hydroxy-5-methylphenyl)propionyloxy]-1,1-dimethylethyl}-2,4,8,10-tetraoxaspiro[5.5]undecane and 1.8% of by-products, but that there is contained no methyl 3-(3-tert-butyl-4-hydroxy-5-methylphenyl)propionate which was the starting material.

EXAMPLES 2 TO 6

Recrystallization was repeated in the same manner as in Example 1 except that cyclohexane was replaced by each of cyclopentane (Example 2), methylcyclopentane (Example 3), methylcyclohexane (Example 4), cyclooctane (Example 5) and cyclododecane (Example 6). The results are shown in Table 2.

EXAMPLES 7 TO 11

Recrystallization was repeated in the same manner as in Example 1 except that the cyclohexane was mixed with 2.5 g of each of methanol (Example 7), ethanol (Example 8), ethyl acetate (Example 9), n-butyl acetate (Example 10) and carbon tetrachloride (Example 11). The results are shown in Table 2.

EXAMPLES 12 AND 13

Recrystallization was repeated in the same manner as in Example 1 except that the highly viscous substance obtained in Reference example 1 was replaced by each of the highly viscous substances obtained in Reference examples 2 (Example 12) and 3 (Example 13) and that the operation was repeated twice. The results are shown in Table 2.

EXAMPLE 14

Fifty grams of the highly viscous substance obtained in Reference example 1 were dissolved in 150 g of a n-hexane/ethyl acetate mixed solvent (weight ratio, 10:1) at 70° C. The resulting solution was rapidly cooled with stirring, and 0.1 g of seed crystals were added at 30° C. Thereafter, the solution was stirred at the same temperature for further 6 hours to form crystals. The crystals were filtered off on a glass filter, washed with n-hexane and dried at 40° C. under reduced pressure to obtain 46.5 g of white crystals having a melting point of 99° to 105° C. Analysis of the white crystals showed that they contained 97.8% of 3,9-bis{2-[3-(3-tert-butyl-4-hydroxy-5-methylphenyl)propionyloxy]-1,1-dimethylethyl}-2,4,8,10-tetraoxaspiro[5.5]undecane and 2.2% of by-products, but that there is contained no methyl 3-(3-tert-butyl-4-hydroxy-5-methylphenyl)-propionate which is the starting material.

EXAMPLES 15 TO 17

Recrystallization was repeated in the same manner as in Example 14 except that n-hexane was replaced by each of n-heptane (Example 15), n-octane (Example 16) and 2-methylheptane (Example 17). The results are shown in Table 2.

EXAMPLE 18

Recrystallization was repeated in the same manner as in Example 14 except that the n-hexane/ethyl acetate mixed solvent was replaced by a n-heptane/n-butanol mixed solvent (weight ratio, 20:1), and that n-heptane was used for washing. The result is shown in Table 2.

EXAMPLES 19 TO 25

Recrystallization was repeated in the same manner as in Example 18 except that n-butanol was replaced by each of carbon tetrachloride (Example 19), chlorobenzene (Example 20), methyl ethyl ketone (Example 21), acetonitrile (Example 22), diethylene glycol (Example 23), toluene (Example 24) and 1,4-dioxane (Example 25). The results are shown in Table 2.

COMPARATIVE EXAMPLE 1

Recrystallization was carried out in the same manner as in Example 1 except that n-hexane was used in place of cyclohexane, and that the seed crystals were added at 50° C. to form the crystals. The result is shown in Table 2.

COMPARATIVE EXAMPLE 2

Recrystallization was carried out in the same manner as in Example 12 except that n-hexane was used in place of cyclohexane. The result is shown in Table 2.

COMPARATIVE EXAMPLE 3

Recrystallization was carried out in the same manner as in Example 13 except that n-hexane was used in place of cyclohexane. The result is shown in Table 2.

The crystals obtained in Example 1 were subjected to Cu-Kα X-ray diffraction, to obtain an X-ray diffraction pattern as shown in FIG. 1. Also, the crystals obtained in Comparative example 1 showed an X-ray diffraction pattern as shown in FIG. 2, and the crystals obtained in Examples 2 to 25 and Comparative examples 2 and 3 showed the same X-ray diffraction pattern as in FIG. 1.

In the drawings, FIGS. 1, 2 and 3 are the X-ray diffraction patterns of the crystals obtained in Example 1 and Comparative example 1 and the highly viscous substance obtained in Reference example 1, respectively.

TABLE 2

|  |  | Weight of crystal (g) | Purity of desired product (wt. %) | Recrystallization solvent | Time required for crystallization (hr) | Color | Melting point (°C.) |
| --- | --- | --- | --- | --- | --- | --- | --- |
| Example | 1 | 47.1 | 98.2 | Cyclohexane | 6 | White | 102–107 |
|  | 2 | 47.5 | 97.8 | Cyclopentane | 6 | White | 100–105 |
|  | 3 | 46.8 | 98.3 | Methylcyclopentane | 6 | White | 100–106 |
|  | 4 | 46.5 | 98.5 | Methylcyclohexane | 6 | White | 101–106 |
|  | 5 | 45.8 | 98.0 | Cyclooctane | 6 | White | 101–107 |
|  | 6 | 46.1 | 98.2 | Cyclodecane | 6 | White | 100–106 |
|  | 7 | 46.5 | 97.5 | Cyclohexane/methanol | 8 | White | 99–105 |
|  | 8 | 45.7 | 97.9 | Cyclohexane/ethanol | 8 | White | 99–105 |
|  | 9 | 46.4 | 98.6 | Cyclohexane/ethyl acetate | 7 | White | 100–105 |
|  | 10 | 45.3 | 98.5 | Cyclohexane/n-butyl acetate | 8 | White | 99–104 |
|  | 11 | 45.1 | 98.2 | Cyclohexane/carbon tetrachloride | 6 | White | 100–105 |
|  | 12 | 31.5*2 | 93.2*1 97.2*2 | Cyclohexane | 24*1 8*2 | White*2 | 102–106*2 |
|  | 13 | 33.9*2 | 93.7*1 97.5*2 | Cyclohexane | 24*1 8*2 | White*2 | 101–106*2 |
|  | 14 | 46.5 | 97.8 | n-Hexane/ethyl acetate | 12 | White | 99–105 |
|  | 15 | 45.9 | 97.9 | n-Heptane/ethyl acetate | 12 | White | 99–105 |
|  | 16 | 46.0 | 97.2 | n-Octane/ethyl acetate | 12 | White | 98–105 |
|  | 17 | 45.3 | 97.5 | 2-Methylheptane/ethyl acetate | 12 | White | 98–105 |
|  | 18 | 45.5 | 97.4 | n-Heptane/n-butanol | 12 | White | 100–105 |
|  | 19 | 45.7 | 97.5 | n-Heptane/carbon tetrachloride | 12 | White | 100–104 |
|  | 20 | 44.5 | 97.9 | n-Heptane/chlorobenzene | 12 | White | 100–105 |
|  | 21 | 44.2 | 97.2 | n-Heptane/methyl ethyl ketone | 12 | White | 101–106 |
|  | 22 | 46.3 | 98.0 | n-Heptane/acetonitrile | 12 | White | 100–105 |
|  | 23 | 43.5 | 97.3 | n-Heptane/diethylene glycol | 12 | White | 100–104 |
|  | 24 | 44.5 | 97.0 | n-Heptane/toluene | 12 | White | 101–105 |
|  | 25 | 45.0 | 97.5 | n-Heptane/1,4-dioxane | 12 | White | 101–106 |
| Comparative example | 1 | 48.5 | 96.7 | n-Hexane | 6*3 | Pale yellow | 93–101 |
|  | 2 | 44.3*2 | 89.5*1 90.3*2 | n-Hexane | 6*1,2,3 | Pale brown*2 | 89–98*2 |
|  | 3 | 44.8*2 | 90.2*1 | n-Hexane | 6*1,2,3 | Pale | 90–100*2 |

TABLE 2-continued

| Weight of crystal (g) | Purity of desired product (wt. %) | Recrystallization solvent | Time required for crystallization (hr) | Color | Melting point (°C.) |
|---|---|---|---|---|---|
| | 91.5*2 | | | yellow*2 | |

*1 After one recrystallization operation.
*2 After two recrystallization operations.
*3 Solidified at the bottom of apparatus and did not disperse.

What is claimed is:

1. A method for the purification of hydroxyphenylpropionic acid ester represented by the structural formula,

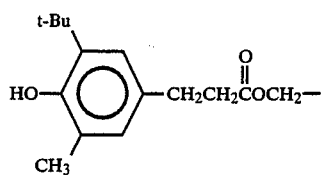

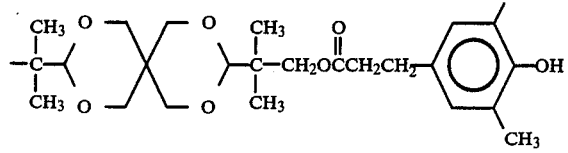

to form crystals thereof having a crystalline structure which, when subjected to Cu-Kα X-ray diffraction, show sharp X-ray diffraction peaks at angles of diffraction, $2\theta=2.8°$, $2\theta=8.7°$ and $2\theta=11.7°$, which comprises recrystallizing the ester at a crystallization temperature lower than 40° C. using as a recrystallization solvent a $C_5$-$C_{10}$ alicyclic hydrocarbon which may or may not contain not more than 5 wt.% of at least one solvent selected from the group consisting of $C_1$-$C_8$ alcohols, $C_3$-$C_8$ carboxylic acid $C_1$-$C_4$ alkyl esters, $C_1$-$C_3$ aliphatic halides, $C_6$-$C_{14}$ aromatic chlorides, $C_3$-$C_{13}$ ketones, $C_2$-$C_3$ aliphatic nitriles, $C_2$-$C_6$ glycols or their $C_1$-$C_4$ alkyl ethers, $C_6$-$C_{14}$ aromatic hydrocarbons and $C_4$-$C_6$ ethers.

2. A purification method as claimed in claim 1, wherein the alicyclic hydrocarbon is cyclohexane.

3. A method for the purification of hydroxyphenylpropionic acid ester represented by the structural formula,

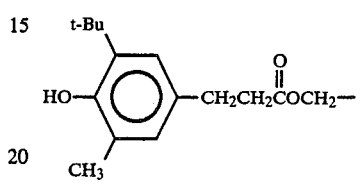

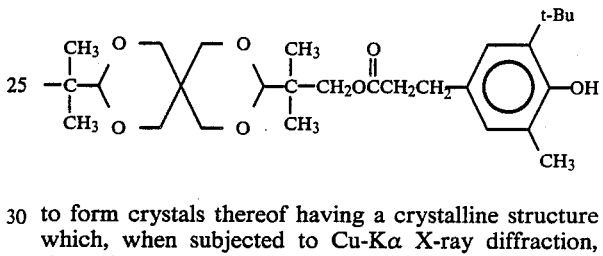

to form crystals thereof having a crystalline structure which, when subjected to Cu-Kα X-ray diffraction, show sharp X-ray diffraction peaks at angles of diffraction, $2\theta=2.8°$, $2\theta=8.7°$ and $2\theta=11.7°$, which comprises recrystallizing the ester at a crystallization temperature lower than 40° C. using as a recrystallization solvent a mixed solvent comprising a $C_5$-$C_{10}$ aliphatic hydrocarbon (III) and at least one solvent (II) selected from the group consisting of $C_1$-$C_8$ alcohols, $C_3$-$C_8$ carboxylic acid $C_1$-$C_4$ alkyl esters, $C_1$-$C_3$ aliphatic halides, $C_6$-$C_{14}$ aromatic chlorides, $C_3$-$C_{13}$ ketones, $C_2$-$C_3$ aliphatic nitriles, $C_2$-$C_6$ glycols or their $C_1$-$C_4$ alkyl ethers, $C_6$-$C_{14}$ aromatic hydrocarbons and $C_4$-$C_6$ ethers, the weight ratio of (III) to (II) being 1000 to 5-100.

4. A purification method as claimed in claim 3, wherein the aliphatic hydrocarbon (III) is n-heptane.

5. A purification method as claimed in claim 3, wherein the aliphatic hydrocarbon (III) is n-hexane.

* * * * *